United States Patent
Vaughan

[11] Patent Number: 5,864,961
[45] Date of Patent: Feb. 2, 1999

[54] URETHRAL PROBE FOR DIAGNOSING STRESS INCONTINENCE

[76] Inventor: Ward P. Vaughan, 115 Old Forest Cir., Winchester, Va. 22602

[21] Appl. No.: 707,708

[22] Filed: Sep. 4, 1996

[51] Int. Cl.⁶ .................................................. A61B 5/103
[52] U.S. Cl. .............................. 33/512; 600/587; 600/591
[58] Field of Search ............................... 33/512; 600/591, 600/587; 606/190, 119

[56] References Cited

U.S. PATENT DOCUMENTS

| | | | |
|---|---|---|---|
| 4,121,572 | 10/1978 | Krzeminski | 33/836 |
| 4,685,474 | 8/1987 | Kurz et al. | 33/512 |
| 5,109,869 | 5/1992 | Buckley | 33/512 |

*Primary Examiner*—Christopher W. Fulton
*Attorney, Agent, or Firm*—William H. Holt

[57] ABSTRACT

An urethral probe comprised of a generally inflexible rod having a length of about 14 to 20 centimeters, extremely smooth surfaces and including a bulbous tip approximately one centimeter in length, an enlarged central portion of approximately 0.5 centimeters in diameter and a rounded terminal end portion. The probe is preferably of molded plastic, packaged in a sterile individual wrapper and disposed of after a single use. Calibrations in hypoallergenic ink assist the doctor or technician in the performance of a "Q-tip test" for measuring the urethral length, for evaluating the tone of the patient's sphincter, i.e., the trigone of the bladder, and for detecting the amount of change in the urethral vesicle angle incident to the diagnosis and evaluation of urinary stress incontinence.

9 Claims, 1 Drawing Sheet

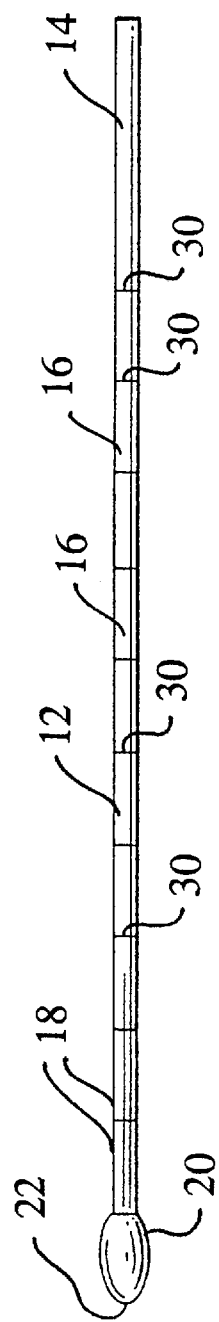
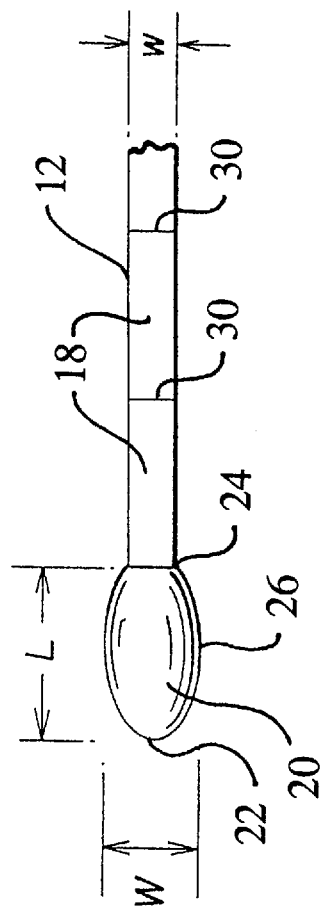

URETHRAL PROBE FOR DIAGNOSING STRESS INCONTINENCE

BACKGROUND OF THE INVENTION

It has been more than 25 years since gynecologists first performed a "Q-tip test" utilizing a cotton-tipped device as an urethral probe for measuring the urethral length and change in the vesicle angle while making a diagnosis and/or evaluation of urinary stress incontinence. This procedure is described in considerable detail in U.S. Pat. No. 4,072,144 granted in 1978 and in U.S. Pat. No. 4,612,939 granted in 1986.

A clinician uses an urethral probe for examining the urethra of a female patient as an aid in determining the extent of relaxation or change in position of the supporting tissues around the neck of the bladder, sphincter (trigone) and urethra.

The probe in the hands of a skilled physician is used to measure the change in the urethral vesicle angle when the patient performs one or more straining maneuvers, and also is used to determine the length of the urethra and the tone of the sphincter, i.e., the trigone of the bladder.

SUMMARY OF THE INVENTION

This invention relates to an urethral probe in the form of a disposable, plastic rod member having particularly smooth surfaces for precluding irritation and possible injury to sensitive tissue. The probe includes an elongate rod having a distal end portion with a bulbous tip portion and a rounded terminal end portion integrally formed, preferably by a molding process for producing smooth surfaces on all portions thereof that will or might come into contact with sensitive areas of the patient. In the event that the molded surfaces are not sufficiently smooth, additional manufacturing processes are utilized to produce enhanced smoothness to avoid the unnecessary trauma, pain and irritation which patients have heretofore suffered when subjected to the standard, cotton-tipped probe that is currently in common use.

The rod member is round in transverse section and provided at its distal end with a very smooth, bulbous tip having a very smooth, rounded terminal end to aid during insertion and to minimize any possible trauma or perforation of the bladder wall or tissue. Further, the bulbous tip also aids in proper positioning of the probe; in use, the bulbous tip is gently advanced past the trigone and then gently retracted until resistance is met, thus accurately positioning the probe prior to the taking of measurements. The proximal end can be of lesser smoothness to provide a surer grip for the user and it will not cause patient trauma.

The probe may be constructed of synthetic polymers, thermoplastics, metal or glass and, preferably, is molded of thermoplastic material so as to be light in weight, is to be provided with a peelable, sterile wrapping (not shown) and is to be disposed of after a single use, thereby providing a safe, convenient and very economical instrument.

Calibrations, including spaced markings and numerals (not shown) are printed in hypoallergenic ink and aid in measuring the length of the urethra.

BRIEF DESCRIPTION OF THE DRAWINGS

FIG. 1 is an elevational view showing the urethral probe.

FIG. 2 is a fragmentary, plan view showing an enlarged portion of the probe and illustrates several important dimensions of a preferred embodiment of the invention.

DESCRIPTION OF THE PREFERRED EMBODIMENT

Referring to the drawings, the urethral probe, generally indicated by the numeral 10, is comprised of an elongate, generally inflexible one-piece rod 12 having a proximal end portion 14, a central portion 16 and a distal end portion 18. It is to be understood that the probe 10 is to be manufactured to have very smooth surfaces at all portions thereof which might possibly come into contact with a patient during an examination procedure; thus, it is likewise an important part of the invention that the probe 10 be formed to be circular in transverse section any where along its length except, perhaps, at the proximal end portion 14 which can have a lesser smoothness for providing an enhanced gripping surface at that end. As mentioned above, smoothness of the probe 10 is a very important feature of the invention in order to avoid subjecting the patient to the trauma induced by conventional cotton-tipped probes, including pain and irritation that has occurred during and following examination procedures in the recent past.

A smooth, bulbous tip portion 20 includes a smooth, rounded terminal end portion 22 and is integrally formed with rod 12 at the distal end portion 18. As is best shown in FIG. 2, bulbous tip portion 20 has a length L, extending from terminal end portion 22 to a line of joinder 24 with rod 12, of approximately one (1) centimeter, and a curved, gradually tapered or rounded surface having a central portion 26 that is approximately one-half (0.5) centimeter in diameter, as is shown by the dimension W at the left portion of FIG. 2. Rod 12 is circular in transverse section throughout tip portion 20 and the distal end portion 18 and has a diameter of approximately three tenths (0.3) centimeter, as is shown by the dimension W at the right portion of FIG. 2. These dimensions provide probe 10 with sufficient rigidity needed during insertion into and withdrawal from a patient's urethra.

Probe 10 is provided along the length of rod 12 with a series of spaced calibrations 30 in the form of ink markings spaced one (1.0) centimeter from each other and made with hypoallergenic ink. While only the calibrations or marks 30 are shown in the drawing, it is to be understood that numerals may also be added for quick measuring purposes and the numerals would increase from the distal end 18 to the proximal end 14.

Purposes and Procedure

Probe 10 has several uses.

Probe 10 will allow the clinician to determine to what extent the supporting tissues around the neck of the patient's bladder, sphincter (trigone) and the urethra relax or change position under stress. Probe 10 aids the skilled clinician in determining the angular change in orientation of the urethral vesicle angle. It is to be understood that an angular change, under stress, on the order of 10 to 20 degrees generally indicates there is no surgically correctable problem. An angular change, under stress, on the order of 25 to 40 degrees is an indication that further examination procedures be performed to determine the cause of the urine loss. An angular change, under stress, of over 45 degrees is a clear indication that surgical corrective treatment would be beneficial to correct the urinary stress incontinence.

Probe 10 will allow the skilled clinician to measure the length of the patient's urethra.

Probe 10 will allow the skilled clinician to evaluate the tone of the patient's urethra, i.e., the trigone of the bladder.

The actual procedure for using urethral probe 10 is essentially the same as with the heretofore conventional Q-tip test. The patient is dressed in an appropriate examining gown and placed upon the examination table in the conventional lithotomy position with her heels comfortably placed in foot stirrups. The urethra is prepped with an antiseptic solution. The examiner, and any nurse or other assistant, use sterile gloves for removing probe 10 from its sterile wrapper. Probe 10 is then inserted by the examining clinician into the patient's urethra until resistance from the trigone is met. Bulbous tip portion 20 is gently advanced past the trigone and then gently retracted until resistance is met, thus placing probe 10 in position for making measurements. The urethral length is read from the calibrated markings 30 and the patient is then asked to perform one or more straining maneuvers. The change in the angle of rod 12 from its original position is visually determined by the examining clinician to note the change in the urethral vesicle angle. Probe 10 is gently withdrawn from the urethra while the clinician notes the resistance of the trigone which will indicate the presence or absence of tone. Using the results of the examination the clinician can then proceed with other tests involved in the evaluation of stress incontinence symptoms.

While the invention has been illustrated and described in the shape and form presently believed to be the best mode of the urethral probe and its manner of use, it is to be understood that various modifications and changes may be made by those skilled in the art without departing from the spirit and scope of the invention as defined by the appended claimed subject matter.

I claim:

1. An urethral probe, said probe comprising an elongate, generally inflexible one-piece rod having a distal end portion and a proximal end portion; said distal end portion having a smooth bulbous tip portion with a smooth rounded terminal end portion; said rod being generally circular in cross-section along its length adjacent to said bulbous tip portion; said rod having a length of at least approximately 14 centimeters and having a diameter of approximately 0.3 centimeters; said bulbous tip portion being integral with said rod, having a length of approximately one centimeter, being circular in transverse cross-section, and having a slightly enlarged central portion of approximately 0.5 centimeters in diameter; said bulbous tip portion gradually increasing in diameter from said rounded terminal end portion to said slightly enlarged central portion and then gradually decreasing in diameter to equal the diameter of said rod.

2. An urethral probe as defined in claim 1 wherein said proximal end portion of said rod is slightly less smooth than the remainder thereof.

3. An urethral probe as defined in claim 1 wherein said rod is marked along its length with spaced calibrations; calibrations being equally spaced one centimeter apart.

4. An urethral probe as defined in claim 3 wherein said calibrations are made with hypoallergenic ink.

5. An urethral probe as defined in claim 1 wherein said rod is constructed in one piece, and wherein said distal end portion, including said bulbous tip portion and terminal end portion, and an adjacent length of said rod each include extremely smooth surfaces.

6. An urethral probe as defined in claim 5 wherein said rod is molded from material selected from the group consisting of synthetic polymers, thermoplastics, metal or glass.

7. An urethral probe as defined in claim 5 wherein said proximal end portion of said rod is slightly less smooth than the remainder thereof.

8. An urethral probe as defined in claim 5 composed of molded thermoplastic material.

9. An urethral probe as defined in claim 1 wherein said rod has a length in the range of 14 to 20 centimeters.

\* \* \* \* \*